United States Patent [19]

Couchman et al.

[11] Patent Number: 4,761,401

[45] Date of Patent: Aug. 2, 1988

[54] OLIGOSACCHARIDES

[75] Inventors: John R. Couchman, Birmingham, Ala.; Walter T. Gibson, Wellingborough, England

[73] Assignee: Lever Brothers Company, New York, N.Y.

[21] Appl. No.: 891,940

[22] Filed: Jul. 29, 1986

[30] Foreign Application Priority Data

Aug. 1, 1985 [GB] United Kingdom ................ 8519416

[51] Int. Cl.$^4$ .................... C07H 1/00; A61K 31/70; A61K 31/72

[52] U.S. Cl. ..................... 514/53; 514/844; 514/880; 536/4.1; 536/21; 536/55.1; 536/115; 536/123

[58] Field of Search ................ 514/53, 880, 844; 536/4.1, 21, 55.1, 115, 123

[56] References Cited

U.S. PATENT DOCUMENTS

| | | | |
|---|---|---|---|
| 4,297,340 | 10/1981 | Abe et al. | 536/115 |
| 4,391,800 | 7/1983 | Durette et al. | 514/885 |
| 4,495,346 | 1/1985 | Anderson et al. | 536/4.1 |
| 4,528,106 | 7/1985 | Grolitzer | 536/4.1 |
| 4,607,025 | 8/1986 | Petitou et al. | 536/123 |
| 4,612,304 | 9/1986 | Fukushi | 536/115 |
| 4,665,060 | 5/1987 | Mardh et al. | 514/53 |

FOREIGN PATENT DOCUMENTS

| | | |
|---|---|---|
| 35919 | 9/1981 | European Pat. Off. |
| 64012 | 11/1982 | European Pat. Off. |
| 84999 | 8/1983 | European Pat. Off. |
| 2438534 | 2/1976 | Fed. Rep. of Germany |
| 59-186911 | of 1984 | Japan |
| 1408036 | 10/1975 | United Kingdom |

OTHER PUBLICATIONS

"J. Biol. Chem.", 240(3), 992–996 (1965) by Olavesen & Davidson.
"Biochim. Biophys. Acts.", 101, 245–251 (1965) by Olavesen & Davidson.
"J. Org. Chem.", 27, 1794–1800 (1962) by Horton & Wolfrom.
"Carbonydrate Research", 40, 23–29 (1975) by David & Veyrieres.
"J. Am. Chem. Soc.", 97, 4063–4068 (1975) by Lemieux & Driguez.
"Proc. Soc. Expl. Biol. Med", 108, 59–63 (1961) by Meyer et al.

*Primary Examiner*—Ronald W. Griffin
*Attorney, Agent, or Firm*—Milton L. Honig; James J. Farrell

[57] ABSTRACT

Esterified oligosaccharides particularly estersified disaccharides containing a uronic acid residue and a hexosamine residue joined through a glycosidic linkage. Such as useful in cosmetic and pharmaceutical compositions.

36 Claims, No Drawings

OLIGOSACCHARIDES

FIELD OF INVENTION

The invention relates to novel oligosaccharides, particularly to esterified disaccharides containing a uronic acid residue and a hexosamine residue joined through a glycosidic linkage. The invention also relates the synthesis of these esterified disaccharides and to their use, particularly in cosmetic and pharmaceutical compositions.

PRIOR ART

Certain α-1,4 esterified disaccharides, together with their synthesis and use in controlling the coagulation of blood, are described by Choay S. A. in EP-A No. 0 064 012. These α-1,4 disaccharides are said to have the structure:

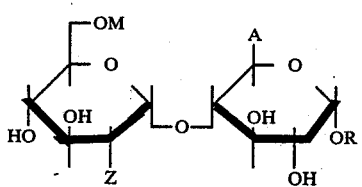
(1)

where
- Z represents a functional nitrogen group, such as an azide or a group having the structure —NHB, in which B represents —H or a functional group such as acetyl or sulphate as a salt with an organic or mineral cation;
- M represents —H or —SO$_3$M$_1$, where M$_1$ is an organic or metallic cation, particularly an alkali metal; or an acetyl group;
- R represents a C$_1$ to C$_4$ alkyl radical, especially methyl; or an aryl radical;
- A represents a functional group such as an acid or —COOR$_1$, where R$_1$ represents —H or a C$_1$ to C$_4$ alkyl radical, especially methyl; or a metal, especially an alkali metal.

COMPOUNDS PER SE

The novel esterified oligosaccharides of the invention differ from the disaccharides described by Choay S. A.

DEFINITION OF THE INVENTION

Accordingly, the invention provides esterified oligosaccharides including at least one esterified disaccharide unit consisting of a uronic acid residue having the structure:

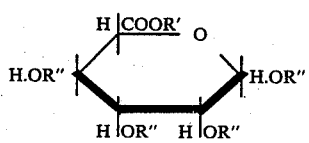
(2a)

and a hexosamine residue having the structure:

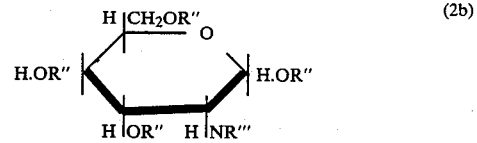
(2b)

where
R' is C$_3$ to C$_{10}$ alkyl or

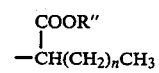

R'' is —H, C$_1$ to C$_4$ alkyl, —CO(CH$_2$)$_m$CH$_3$, —SO$_3$M,

R''' is —H, —CO(CH$_2$)$_m$CH$_3$, or —SO$_3$M,

M is —H, or a metallic or organic cation n is 0 or an integer of from 1 to 7, and m is 0 or the integer 1 or 2;

the groups designated R'' being the same or different, one R'' group from each pyranose ring structure being linked by a glycosidic linkage having the configuration α-1,3; α-1,4; β-1,3 or β-1,4; and the —COOR', —CH$_2$OR'' and —OR'' groups being of either configuration with respect to the pyranose rings; provided that when the esterified oligosaccharide is an esterified disaccharide unit having the structure:

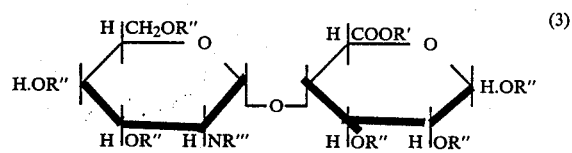
(3)

then R' is C$_5$ to C$_{10}$ alkyl or

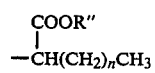

THE ESTERIFIED OLIGOSACCHARIDE

The esterified oligosaccharide according to the invention can comprise from 2 to 8, preferably from 2 to 4 saccharide residues, of which at least two saccharide residues form the esterified disaccharide unit as herein defined.

Preferably, the esterified oligosaccharide is an esterified disaccharide consisting of a uronic acid residue having the structure (2a) linked via a glycosidic linkage to a hexosamine residue having the structure (2b).

Particularly preferred examples of the esterified disaccharides of the invention have the following structures, where the designation of R', R'', R''' and are as hereinbefore defined.

A first generic structure is:

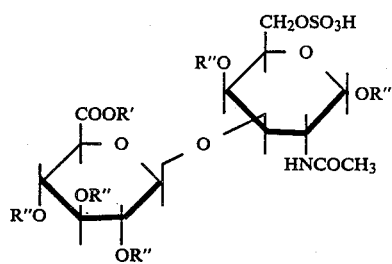
Specific examples of the esterified disaccharide (4) have the structures shown as (5), (6), (7) and (8).
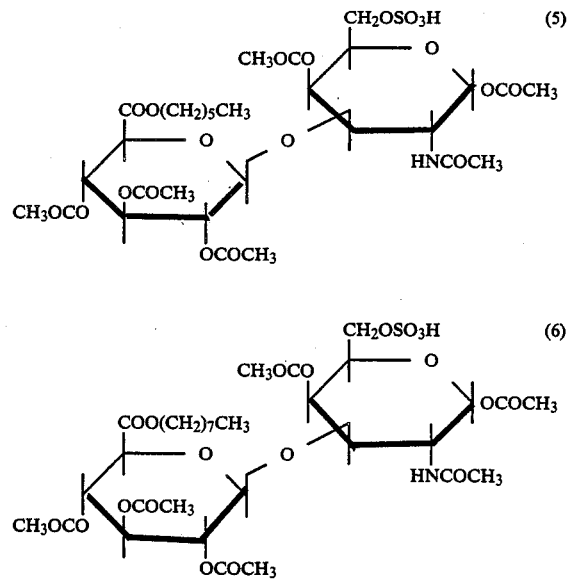
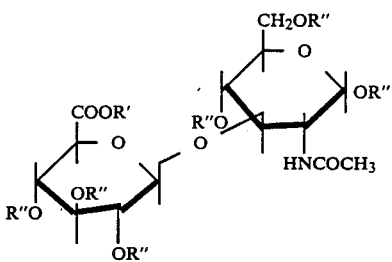
Specific examples of the esterified disaccharide (9) have the structures shown in (10) and (11).
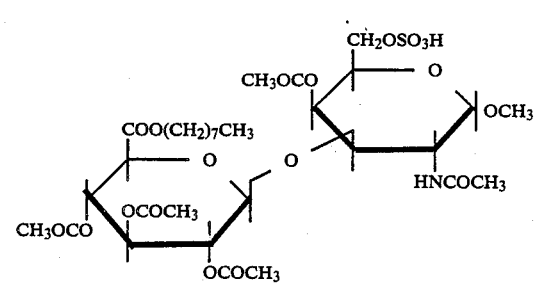
A further generic structure is:
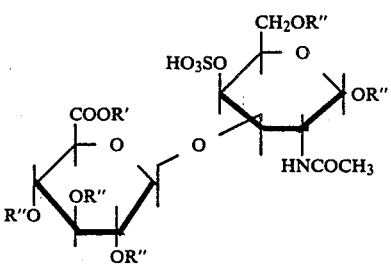
A specific example of the esterified disaccharide (12) has the structure shown in (13).
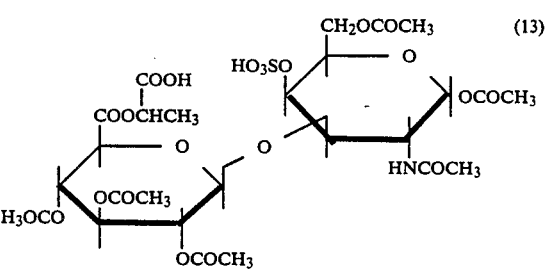
A further generic structure is:
A further generic structure is:

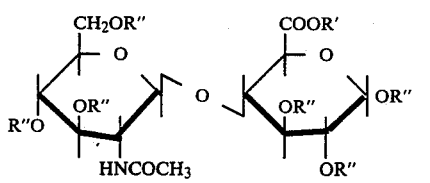 (14)

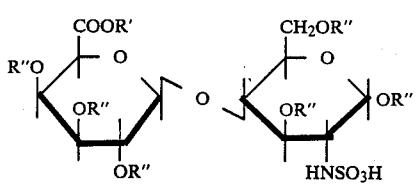 (19)

A specific example of the esterified disaccharides (14) has the structure shown in (15)

A specific example of the esterified disaccharide (19) has the structure shown in (20).

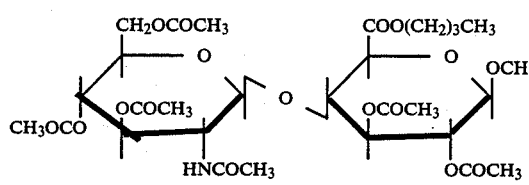 (15)

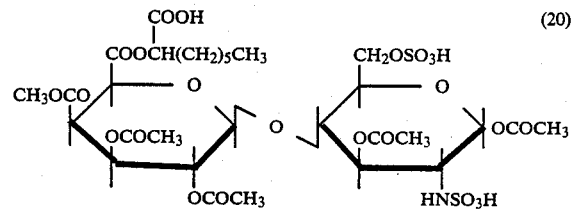 (20)

A further generic structure is:

A further generic structure is:

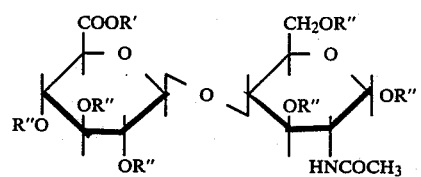 (16)

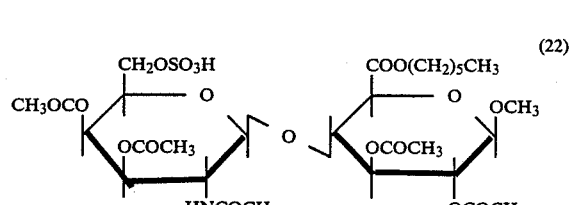 (21)

Specific examples of the esterified disaccharide (16) have the structures shown in (17) and (18).

A specific example of the esterified disaccharide (21) has the structure shown in (22):

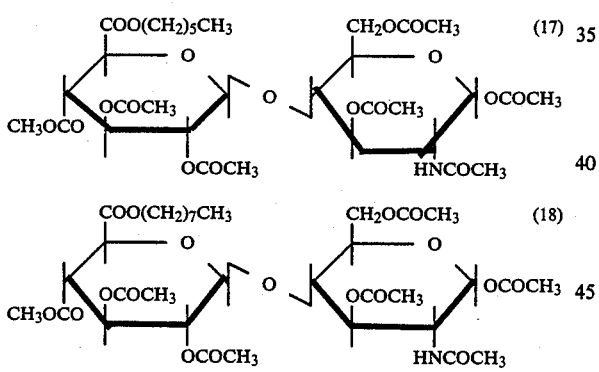 (17) (18)

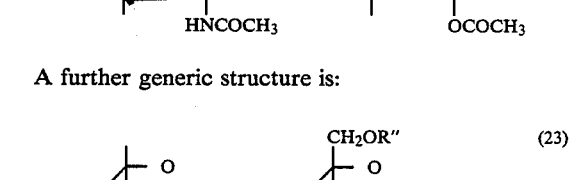 (22)

A further generic structure is:

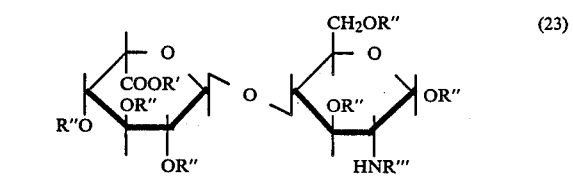 (23)

A further generic structure is:

Specific examples of the esterified disaccharide (23) has the structures shown in (24) and (25).

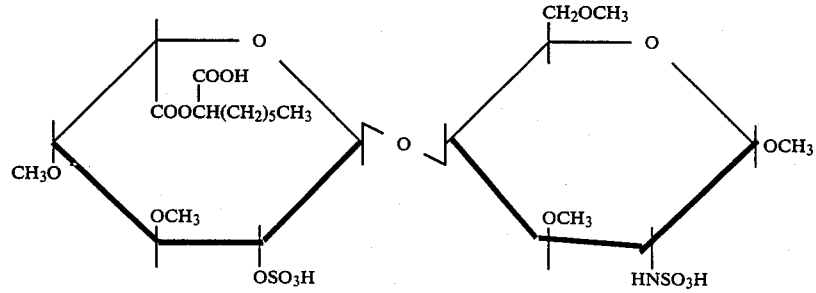 (24)

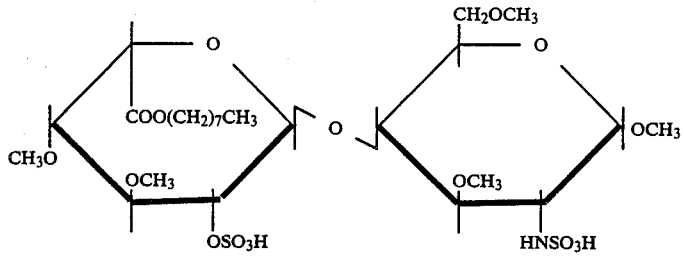
(25)

A further generic structure is:

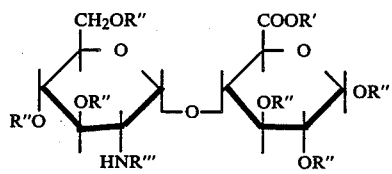
(26)

A specific example of the esterified disaccharide (26) has the structure shown in (27).

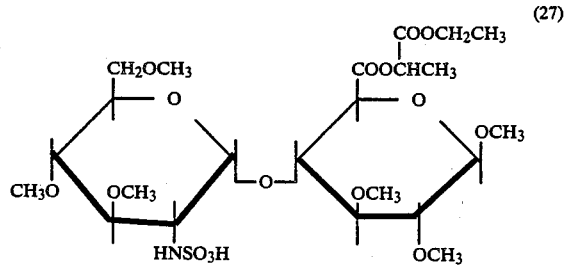
(27)

A further generic structure is:

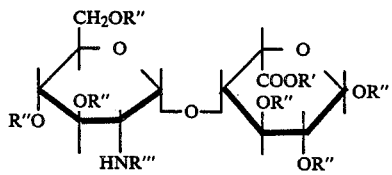
(28)

A specific example of the esterified disaccharide (28) has the structure shown in (29).

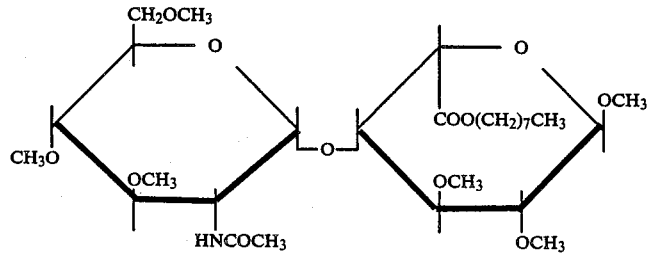
(29)

SYNTHESIS OF THE NOVEL ESTERIFIED OLIGOSACCHARIDES

Two possible routes for synthesising the novel esterified oligosaccharides according to the invention are envisaged.

1. Hydrolysis of polysacchrides

Intact glycosaminoglycan chains can be subjected to partial hydrolysis to yield oligosaccharides comprising at least one disaccharide having a uronic acid residue linked to a hexosamine residue. These oligosaccharides can then be modified to provide the corresponding esterified oligosaccharides of the invention. This synthesis is particularly suited to the production of esterified oligosaccharides having the structures of the generic types (4), (9) and (12).

DEFINITION OF THE INVENTION

Accordingly, the invention provides a process for the synthesis of an esterified oligosaccharide having a generic structure chosen from structures (4), (9) and (12), which comprises the steps of:

(i) Subjecting a glycosaminoglycan chain to chemical cleavage to yield oligosaccharide fragments containing at least one disaccharide unit comprising a hexosamine residue having the structure:

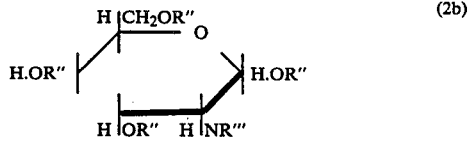
(2b)

which is glysocidically linked to the C-1 position of a uronic acid residue having the structure:

(2a)

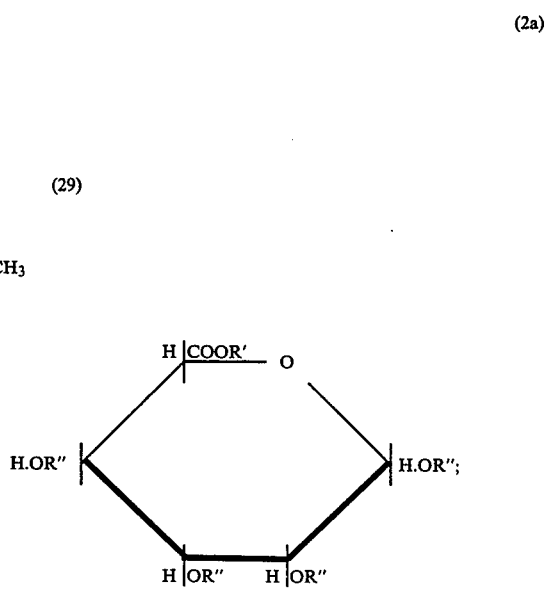

(ii) modifying the oligosaccharide by at least one process step chose from:
acylation of free hydroxyl groups,
acylation of free amino groups,
sulphation of free hydroxyl groups,
sulphation of free amino groups,
esterification of free hydroxyl groups, and
esterification of free hydroxyl groups,
to provide a structure of the generic type chosen from structures (4), (9) and (12).

Preferred glycosaminoglycan chains which form the starting materials for this synthesis are chondroitin sulphate and hyaluronic acid.

Of the modifying steps which can be applied to the oligosaccharide in order to obtain the esterified oligosaccharide of the invention, it is preferred that these are carried out in a stepwise fashion to acylate the 2-amino group of the hexosamine moiety to esterify or acrylate the remaining free hydroxyl groups and to esterify the carboxyl group on the uronic acid moiety.

Chemical cleavage of the intact glycosaminoglycan chains is preferably achieved by acid hydrolysis or enzymic digestion.

In order to illustrate Method 1, the synthesis of the esterified disaccharide having the structure (5) starting from chondroitin sulphate is now described.

The disaccharide chondrosine (30) was obtained from chondroitin sulphate by acid hydrolysis. 10 g of chondroitin sulphate was hydrolysed with 200 ml of 2N sulphuric acid by refluxing at 100° C. for 4 hours. The resulting hydrolysate was chromatographed on Dowex 50W-X-8 (200-400 mesh) resin in the hydrogen form. The column was eluted with 0.2N sulphuric acid and all fractions were tested with ninhydrin/ferric chloride reagent. The first large, broad peak gave a yield of chondrosine after neutralisation with saturated barium hydroxide and lyophilisation to a dry powder.

The method employed was that described in Olavesen & Davidson, J. Biol. Chem. 240(3), 992–996 (1965).

The method employed was that described by Olavesen & Davidson, Ibid.

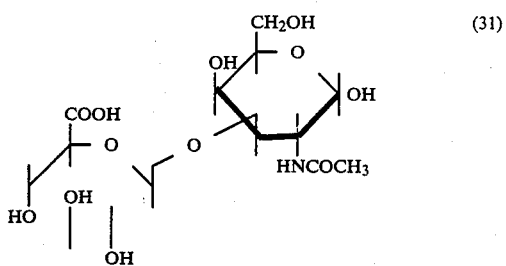
(31)

Sulphation of the product in the C-6 position of the hexosamine moiety was achieved by using triethylamine-N-sulphonic acid. To a mixture of 5 ml dimethylformamide, 7.5 ml benzene and 0.5 ml pyridine was added 500 mg of N-acetylchondrosine after it had been evaporated several times from dry benzene. 9.12 mg of triethylamine-N-sulphonic acid was added and the reaction vessel shaken for 26 hours at room temperature. The resulting solution was evaporated at reduced pressure to a yellow syrup (bath temp. <50° C.) which was extracted with 2×5 ml ether. The resulting oil was extracted with 10 ml chloroform to remove any residual sulphonic acid. Chloroform washings and insoluble solids were washed in situ with 4×5 ml water. The water fractions were combined and lyophilised to give N-acetyl chondrosine-6-O-sulphate (32), as a white fluffy solid which was characterised by I.R. and N.M.R. and by T.L.C.

The method employed was that described by Olavesen & Davidson, Biochim. Biophys. Acta., 101, 245-251 (1965).

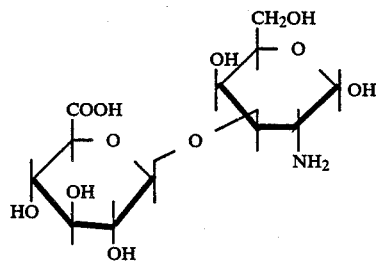
(30)

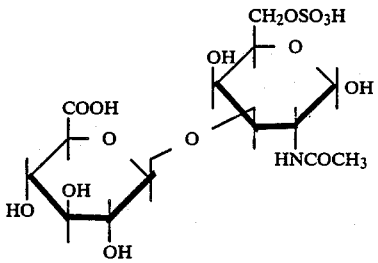
(32)

N-acetylchondrosine (31) was prepared by selective N-acetylation of chondrosine using acetic anhydride. 500 mg chondrosine was dissolved in 500 ml of bicarbonate buffer and cooled to 0°-5° C. (Bicarbonate buffer was prepared by mixing 10 ml 0.1M Na$_2$CO$_3$ and 90 ml 0.1M NaHCO$_3$ having a pH value of 9. To this was added 0.22 ml of acetic anhydride with stirring. The mixture was then left standing at 0° C. overnight. It was then added to a Dowex 50W-X-8 (200-400) column in the acid form. Elution with three bed volumes of distilled water and lyophilisation of the aqueous eluate produced a white fluffy solid which was characterised as N-acetylchondrosine by I.R. and N.M.R. spectroscopy.

The N-acetyl chondrosine-6-O-sulphate (32) was esterified using a modified Pummerer reaction. 500 mg N-acetylchondrosine 6-O-sulphate was added to a large round bottomed flask containing 5 ml of hexanol and 3.4 g of Amberlite IR-120 resin in the hydrogen form. The mixture was refluxed at 100° C. for 4 hours and then the reaction was forced to completion by distillation of the hexanol and formed water. The residual resin was removed by filtration and washing with water. The product having the structure (33) was obtained by lyophilisation and was characterised by I.R., N.M.R. and T.L.C.

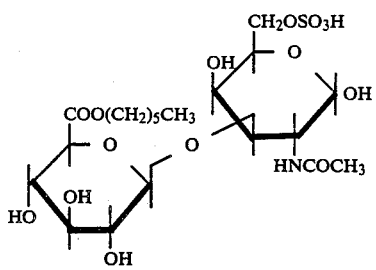

(33)

The fully acetylated disaccharide (5) was prepared using the acetic anhydride/pyridine reagent. 500 mg N-acetylchondrosine-6-O-sulphate-C$_6$ester was dissolved in 30 ml dry pyridine and to this was added 20 ml acetic anhydride. The mixture was then cooled to 0° C. and stirred until all the disaccharide had dissolved. It was then stirred at room temperature for 48 hours. The resulting brown solution was poured into 300 ml of iced water which was extracted with 3×50 ml chloroform. Chloroform solution was evaporated to dryness under reduced pressure at 45° C. to give a yellow syrup. This was treated with ethanol to give an amorphous solid which was subsequently eluted with ethyl acetate from a silicic acid column and lyophilised to produce an amorphous white powder.

The method employed was that employed by Olavesen & Davidson, J. Biol. Chem. 240(3), 992–996 (1965).

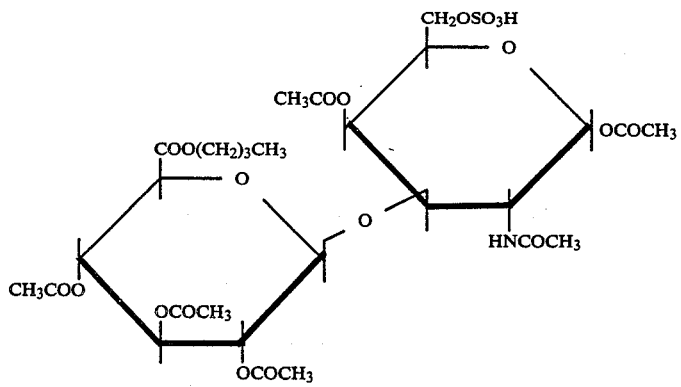

(5)

2. Condensation of uronic acid and hexosamine residues

Esterified oligosaccharides according to the invention having at least one uronic acid residue linked to the β configuration through the C-1 position to a hexosamine residue, or certain esterified oligosaccharides according to the invention having at least one hexosamine residue linked to the α or β configuration through the C-1 position to a uronic acid residue, can be prepared by condensation of relevant uronic acid and hexosamine residues. This synthesis is particularly suited to the production of esterified oligosaccharides having the structures of the generic types (14), (16), (19), (21), (23), (26) and (28).

DEFINITION OF THE INVENTION

Accordingly, the invention also provides a process for the synthesis of an esterified oligosaccharide having at least one uronic acid residue linked in the β configuration through the C-1 position to a hexosamine residue, or having at least one hexosamine residue linked to the α or β configuration through the C-1 position to a uronic acid residue, which process comprises the steps of:

(i) condensing a hexosamine residue having the structure:

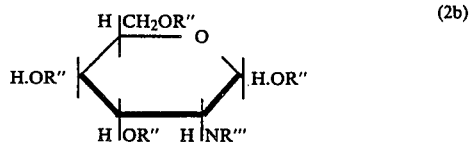

(2b)

with a uronic acid residue having the structure:

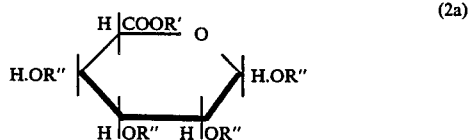

(2a)

to form an oligosaccharide intermediate, the functional groups of which residues have been modified or protected in such a way that glycosidic bond formation can only occur between the C-1 position of one residue and a free hydroxyl group in the C-3 or C-4 position of the other residue, the α or β configuration of the glycosidic linkage so formed being dictated by the nature of the leaving group on the C-1 position; and (ii) removal of at least one protecting group from the oligosaccharide intermediate by one or more process steps in any sequence chosen from:
reduction,
acid catalysis, and
base catalysis;
to provide the esterified oligosaccharide.

It is preferred that this process further comprises modifying the oligosaccharide intermediate by one or more process steps in any sequence, chosen from:
acylation of free hydroxyl groups
acylation of free amino groups
sulphation of free amino groups
esterfication of free hydroxyl groups, and
etherification of free hydroxyl groups.

In order to illustrate Method 2, the synthesis of the esterified disaccharide having the structure (15) by condensation of monosaccharides is now described.

The esterified disaccharide having the structure (15) was prepared by condensation of monosaccharides (34) and (35), as shown below, to give the (β-1,4) disaccharide (36):

(35) was synthesised by esterification, with n-butanol in the presence of sulphuric acid, of the sodium salt of the corresponding uronic acid. The latter was prepared as described in No. EP-A-0 084 999 and No. EP-A-0 064 012.

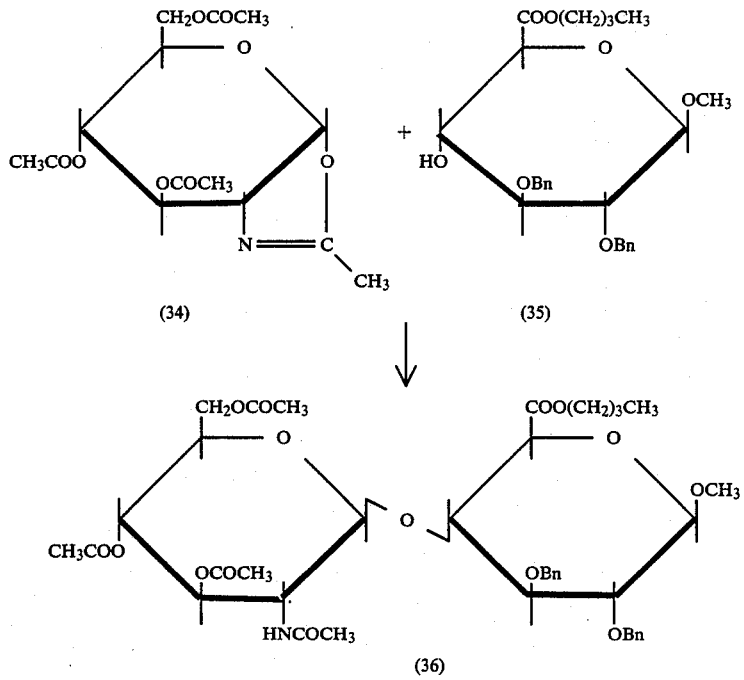

The preparation of (34), the oxazoline derivative of N-acetylglucosamine, was by reaction of N-acetyl glucosamine with acetyl chloride by the method described by Horton & Wolfrom in J. Org. Chem. 27, 1794 (1962), to insert an α-Cl at the C-1 position, followed by oxazoline formation in the presence of tetraethylammonium chloride by the method described by Lemieux & Driguez J. Am. Chem. Soc. 97, 4063 (1975). The oxazoline was a syrup having an $[\alpha]_D$ of $+10°$. Compound Condensation of (34) and (35) was carried out in the presence of nitromethane and p-toluenesulphonic acid as described by David & Veyrieres in Carbohydrate Research 40, 23 (1975). This paper also provided the method for the reduction of (36) by hydrogenation using palladium on carbon as catalyst, to give compound (37):

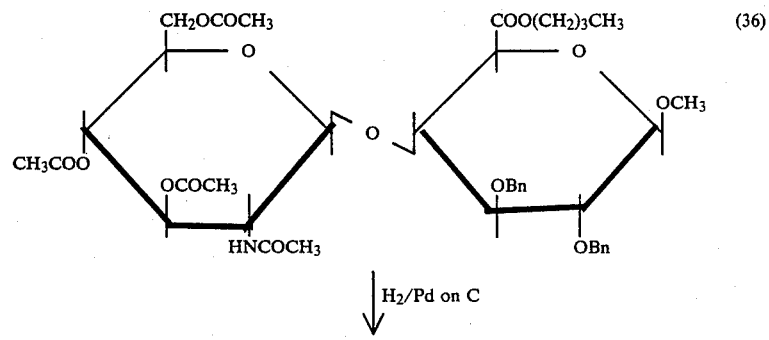

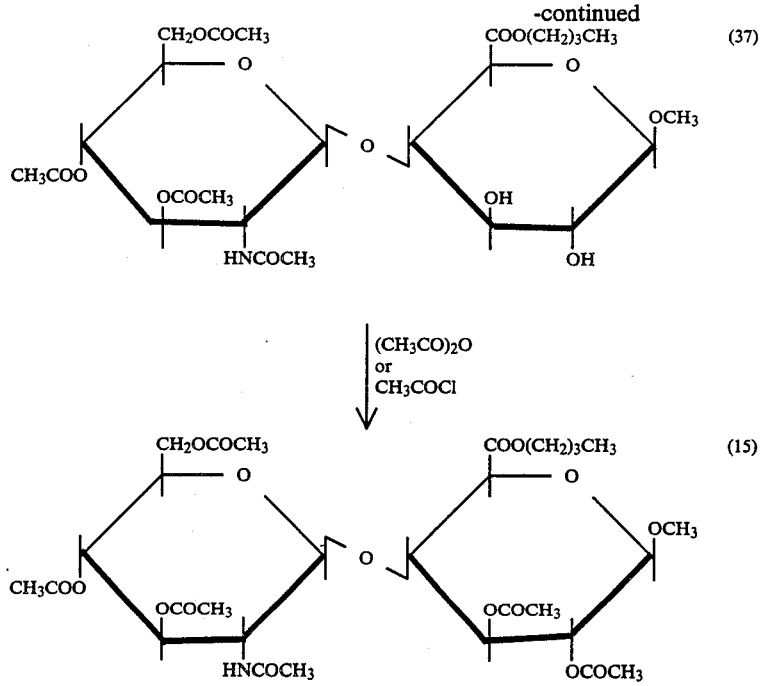

The final step, yielding disaccharide (15) was acetylation of the remaining two ring hydroxyl groups on structure (37) by conventional methods using either acetic anhydride or acetylchloride.

Method 2 can also be illustrated with reference to the synthesis of the esterified disaccharide (22) by condensation of monosaccharides as follows. 1

A similar sequence of reactions as described for disaccharides (15) was followed to prepare disaccharide (22) except that in this case the oxazoline derivative of N-acetyl galactosamine (38) was prepared and condensed with the hexyl ester (39) shown below:

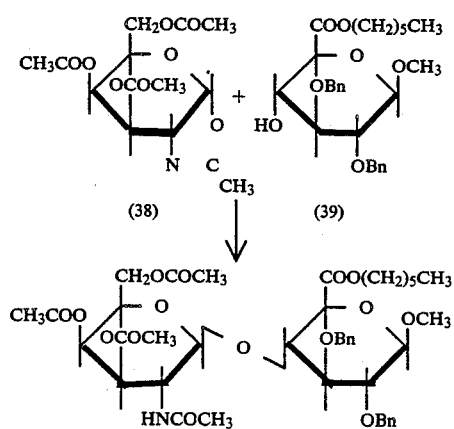

Disaccharide (40) was deacetylated with sodium methoxide and then reduced as described in the synthesis of disaccharide (5) above to remove the benzyl protecting groups. The resulting disaccharide was sulphated in the C-6 position by the method described above for disaccharide (5). Finally, remaining free hydroxyl groups were acetylated to yield disaccharide (22):

COSMETIC AND PHARMACEUTICAL COMPOSITIONS CONTAINING ESTERIFIED OLIGOSACCHARIDES

The invention also relates to cosmetic and pharmaceutical compositions for topical application to mammalian skin containing novel esterified oligosaccharides, particularly esterified disaccharides, as hereinbefore described, and other esterified disaccharides such as those disclosed by Choay S. A. in No. EP-A-0 064 012. These compositions are particularly useful in promoting or enhancing the growth of hair, more particularly on the human scalp.

THE HAIR GROWTH CYCLE

It should be explained that in most mammals, hair does not grow continuously, but undergoes a cycle of activity involving alternate periods of growth and rest. The hair growth cycle can be divided into three main stages, namely:

(i) the growth phase known as anagen, during which the hair follicle penetrates deep into the dermis with the cells of the bulb dividing rapidly and differentiating to form the hair, (ii) the transitional stage known as catagen which is heralded by the cessation of mitosis, and during which the follicle regresses upwards through the dermis and hair growth ceases, (iii) the resting stage known as telogen in which the regressed follicle contains a small secondary germ with an underlying ball of tightly packed dermal papilla cells.

The initiation of a new anagen phase is revealed by rapid cell proliferation in the germ, expansion of the dermal papilla and elaboration of basement membrane components. The hair cycle is then repeated many times until, most of the hair follicles spend an increasing proportion of their time in the telogen stage, and the hairs produced become finer, shorter and less visible; this is known as terminal to vellus transformation. In the human male subject this consequence is seen as the onset of male pattern baldness.

ALLEGED BALDNESS CURES

Although there have been many claims in the scientific literature to the promotion or maintenance of hair growth or regrowth, by the topical application of hair tonics and the like, particularly in the human male subject, none has yet been widely accepted by the consumer as being both safe and effective. Perhaps the only means which has met with partial success for growing hair on the bald or balding human head is by transplantation of hair to the bald areas. This is however an extremely painful operation and is not always successful. Furthermore, it is immediately apparent to the casual observer that the subject has received a hair transplant, and it may take many months or even years before hair regrowth, following this operation, assumes an appearance which resembles that of the original naturally growing hair.

Among the many hair regrowth studies that have been reported in the literature, the work of Meyer et al (1961) in the Proceedings of the Society of Experimental and Biological Medicine, 108, 59–63, is worthy of mention. Meyer and his co-workers repeatedly injected acid mucopolysaccharides intracutaneously into the skin of shaved rabbits and reportedly observed initiation of the hair growth cycle with stimulation of hair growth which in some instances appeared to be thicker than usual. They found that heparitin (also known as heparan) sulphate was particularly active, while dermatan sulphate and chondroitin-6-sulphate were also active in this respect, but to a lesser extent.

It has also been reported by Frajdenrajch in No. EP-A-0 035 919 to include chondroitin sulphate in a hair composition in order to prevent loss and encourage growth of the hair.

Also, Shansho Seijaku in JA-59/186911 describe a shampoo containing a mucopolysaccharide such as chondroitin sulphate.

There are other references, mainly of Japanese origin, which claim the use of chondroitin sulphate in preparations for topical application to human skin, particularly as hair tonics.

FIELD OF THE INVENTION

It is believed that molecules having a molecular weight of greater than about 1500 are unlikely to penetrate skin to any significant extent when applied topically, and accordingly, it is unlikely that polysaccharides such as chondroitin sulphate having a molecular weight of many thousands could penetrate the skin of the scalp, following topical application, and diffuse into the immediate environment of the hair follicle in order to initiate or enhance hair growth. It has however now been discovered that esterified oligosaccharides of smaller molecular weight, including both the novel esterified oligosaccharides according to the invention, and certain related disaccharides which are known for use in compositions other than for the treatment of baldness, can diffuse through the outer layers of the skin to the immediate environment of the hair follicle, where they can positively increase hair growth.

It has accordingly been shown that application of these materials to mammalian skin in the region of vellus hair can convert vellus hair to growth as terminal hair. It has also been shown that the rate of terminal hair growth in mammalian species can be increased by applying these materials to mammalian skin in the region of terminal hair.

It has also been shown that the molecular charge and polarity of a selected esterified oligosaccharide will influence its skin penetration. Accordingly, it is apparent that the more polar or highly charged the esterified oligosaccharide, the less likely it is to penetrate the skin, and for this reason it is advantageous to employ oligosaccharides for this purpose which are esterified to an extent that will reduce their molecular charge. The preferred esterified disaccharides that are selected for optimum penetration of the skin of the scalp are those which have at least 2, most preferably at least 6 ester groups per molecule.

DEFINITION OF THE INVENTION

The invention accordingly also provides compositions suitable for topical application to mammalian skin, particularly to the human scalp, which compositions comprise an oligosaccharide containing hexosamine and uronic acid residues, or mixtures of such oligosaccharides together with a cosmetically and physiologically acceptable vehicle.

THE TOPICAL COMPOSITION

The composition is preferably one comprising one or more esterified oligosaccharides or related disaccharides and a solid, semi-solid or liquid physiologically acceptable vehicle. The nature of the vehicle employed in the preparation of any particular composition will depend on the method intended for administration of that composition. The vehicle can be inert or can possess physiological or pharmaceutical benefits of its own.

The relative amounts of the esterified oligosaccharide of the invention, or related disaccharide, and the vehicle is unimportant, as all that is necessary is the supply of an effective amount of the oligosaccharide or disaccharide for the purpose for which it is administered, the vehicle merely acting as a carrier or diluent of these materials.

THE OLIGOSACCHARIDE

The oligosaccharide that can be incorporated into the composition according to the invention can be one or more of the novel esterified disaccharides as described hereinbefore.

It is also possible to employ esterified oligosaccharides containing three of four or more than four esterified saccharide units, although it is apparent that molecules containing more than four esterified saccharide units may present difficulties, as has been stated earlier, in penetrating the skin to reach the immediate environment of the hair follicle, in view of their excessively large molecular size.

Also suitable for use in the compositions according to the invention are oligosaccharides, especially esterified disaccharides, which are known per se, including those disclosed in No. EP-A-0 064 012 to Choay S. A., but with a disclosed utility other than for the promotion of hair growth or regrowth.

Examples of such esterified disaccharides described by Choay S. A. are those consisting of a uronic acid residue having the structure:

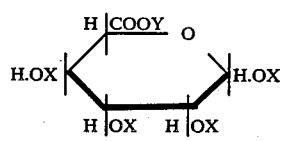 (50)

and a hexosamine residue having the structure:

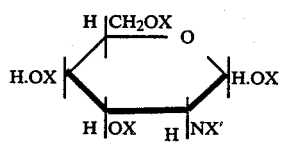 (51)

where
X is —H, $C_1$ to $C_4$ alkyl or an aryl radical, —CO(CH$_2$)$_m$CH$_3$, or —SO$_3$M,
X' is —H, —CO(CH$_2$)$_m$CH$_3$, or —SO$_3$M,
Y is —H, $C_1$ to $C_4$ alkyl, or M
M is —H, or a metallic or organic cation,
m is 0 or the integer 1 or 2;
the groups designated X being the same or different, one —OH group from each pyranose ring structure being linked by a glycosidic linkage having the configuration α-1,3 β-1,3 α-1,4 or β-1,4; and the —COOY, —CH$_2$OX, and —OX groups being of either configuration with respect to the pyranose ring.

Particularly preferred examples of known esterified disaccharides which can be incorporated into compositions according to the invention have the following structures where the designation of X, X', Y and M are as hereinbefore defined.

A generic structure of a known esterified disaccharide based on those disclosed in No. EP-A-0 064 012 to Choay S. A. is:

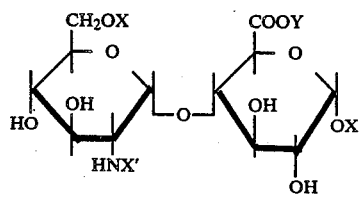 (52)

Specific examples of the esterified disaccharide (52) have the structures shown as (53) to (59).

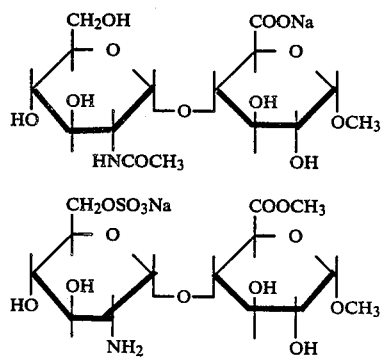

(53)

(54)

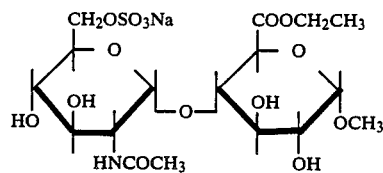 (55)

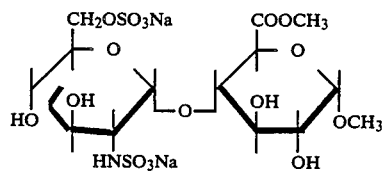 (56)

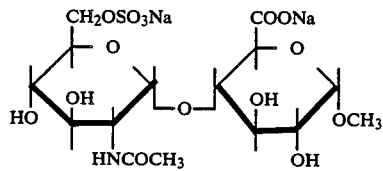 (57)

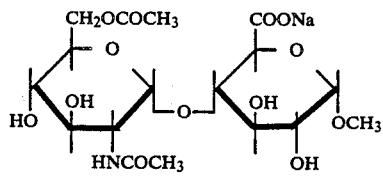 (58)

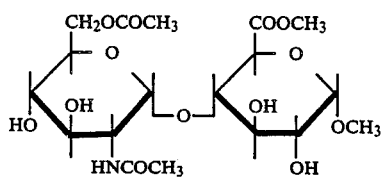 (59)

Specific examples of further esterified disaccharides similar to but not included in the disclosure of No. EP-A-0 064 012 to Choay S. A., have the structures shown on (60) to (63):

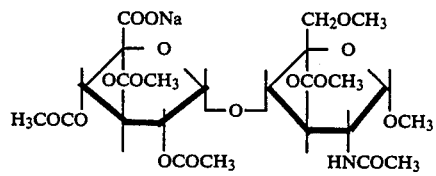 (60)

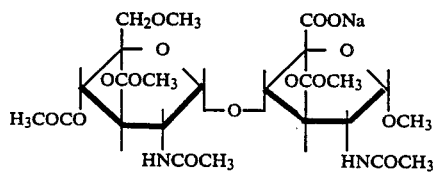 (61)

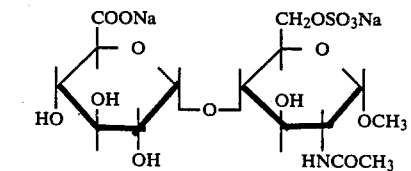 (62)

-continued

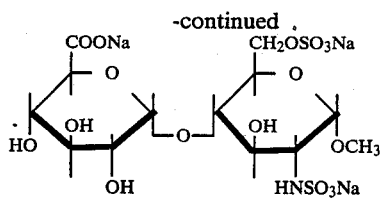

Also suitable for use in compositions according to the invention are oligosaccharides produced by chemical cleavage of glycosaminoglycans, especially chondrosine, having the structure (30), which can be obtained by acid hydrolysis of chondroitin sulphate, and its N-acetyl, and its N-acetyl, O-sulpho derivatives, having the structures (31) and (32) respectively.

Also suitable for use in compositions according to the invention are low molecular weight limit digests of heparan sulphate, hyaluronic acid and chondroitin sulphate produced by the relevant enzyme, namely heparitinase, hyaluronidase and chondroitinase.

Also suitable for use in compositions according to the invention is hyalobiouronic acid having the structure:

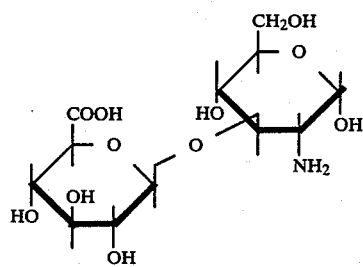

Particularly preferred examples of novel esterified disaccharides according to the invention which can be incorporated into compositions according to the invention have the structures as shown in hereinafter as (5), (6), (7), (8), (10), (11), (13), (15), (17), (18), (20), (22), (24), (25), (27), (29), (30), (31) and (32).

Especially preferred examples of novel esterified oligosaccharides according to the invention, and related disaccharides, which can be incorporated into compositions according to the invention have structures shown hereinbefore as (5), (15), (22) and (31).

The amount of the esterified oligosaccharide to be incorporated with a suitable vehicle into compositions for topical use can vary widely, but in general, an amount of from 0.01 to 10%, preferably from 0.1 to 5% by weight of the composition will provide an adequate dose to the skin after topical application.

THE VEHICLE

The composition should also comprise a cosmetically or physiologically acceptable vehicle to enable the esterified oligosaccharide to be conveyed to the skin in an appropriate dilution.

The selection of a vehicle for this purpose presents a wide range of possibilities depending on the required product form of the composition. Suitable vehicles can be classified as described hereinafter.

It should be explained that vehicles are substances which can act as diluents, dispersants, or solvents for the esterified oligosaccharide and which therefore ensure that it can be applied to and distributed evenly over the hair and/or scalp at an appropriate concentration. The vehicle is preferably one which can aid penetration of the esterified oligosaccharide into the skin to reach the immediate environment of the hair follicle. Compositions according to this invention can include water as a vehicle, and/or at least one cosmetically acceptable vehicle other than water.

Vehicles other than water that can be used in compositions according to the invention can include solids or liquids such as emollients, solvents, humectants, thickeners and powders. Examples of each of these types of vehicles, which can be used singly or as mixtures of one or more vehicles, are as follows:

Emollients, such as stearyl alcohol, glyceryl monoricinoleate, glyceryl monostearate, propane-1,2-diol, butane-1,3-diol, mink oil, cetyl alcohol, isopropyl isostearate, stearic acid, isobutyl palmitate, isocetyl stearate, oleyl alcohol, isopropyl laurate, hexyl laurate, decyl oleate, octadecan-2-ol, isocetyl alcohol, cetyl palmitate, dimethylpolysiloxane, di-n-butyl sebacate, isopropyl myristate, isopropyl palmitate, isopropyl stearate, butyl stearate, polyethylene glycol, triethylene glycol, lanolin, castor oil, acetylated lanolin alcohols, petroleum, mineral oil, butyl myristate, isostearic acid, palmitic acid, isopropyl linoleate, lauryl lactate, myristyl lactate, decyl oleate, myristylmyristate;

Propellants, such as trichlorofluoromethane, dichlorodifluoromethane, dichlorotetrafluoroethane, monochlorodifluoromethane, trichlorotrifluorethane, propane, butane, isobutane, dimethyl ether, carbon dioxide, nitrous oxide;

Solvents, such as ethyl alcohol, methylene chloride, isopropanol, castor oil, ethylene glycol monoethyl ether, diethylene glycol monobutyl ether, diethylene glycol monoethyl ether, dimethyl sulphoxide, tetrahydrofuran;

Humectants, such as glycerin, sorbitol, sodium 2-pyrrolidone-5-carboxylate, soluble collagen, dibutyl phthalate, gelatin;

Powders, such as chalk, talc, fullers earth, kaolin, starch, gums, colloidal silicon dioxide, sodium polyacrylate, tetra alkyl and/or trialkyl aryl ammonium smectites, chemically modified magnesium aluminium silicate, organically modified montmorillonite clay, hydrated aluminium silicate, fumed silica, carboxyvinyl polymer, sodium carboxymethyl cellulose, ethylene glycol monostearate.

The amount of vehicle in the composition, including water if present, should preferably be sufficient to carry at least a portion of the esterified oligosaccharide to the skin in an amount which is sufficient effectively to enhance hair growth. The amount of the vehicle can comprise the balance of the composition, particularly where little or no other ingredients are present in the composition can accordingly comprise from 10 to 99.99%, preferably from 50 to 99.5% and ideally from 90 to 99% by weight of the vehicle or vehicles.

PERFUME

The composition according to the invention can also optionally comprise a perfume in an amount sufficient to make the composition acceptable to the consumer and pleasant to use. Usually, the perfume will form from 0.01 to 10% by weight of the composition.

ACTIVITY ENHANCER

The composition according to the invention can also optionally comprise an activity enhancer whose presence further improves the delivery to the skin of the esterified oligosaccharide. The activity enhancer accordingly effectively increases the partition of the esterified oligosaccharide into the skin from the composition when applied topically.

While screening a series of non-electrolytes for their ability to function as activity enhancers, it was observed that they were all compounds which were capable of substantially increasing the cloud point temperature of nonionic surfactants. Such compounds included short chain alkanols, diols and short chain fatty acids. By contrast, other non-electrolytes which reduce the cloud point temperature of nonionic surfactants, such as long chain alcohols, for example, butan-1-ol and cyclohexanol; polyols, for example sorbitol and propan-1,2,3-triol, do not function as activity enhancers.

An activity enhancer is accordingly defined as a non-electrolyte which is capable, at a concentration of 5% by weight of increasing the cloud point temperature of a 0.025M aqueous solution of polyoxyethylene(8)nonylphenyl ether by at least 10° C. Preferably the activity enhancer is one which is capable of increasing the cloud point temperature by at least 15° C., most preferably by at least 20° C.

It should be explained that the "cloud point" is a measure of the inverse solubility of a nonionic surfactant with temperature and can be determined by heating a standard clear aqueous solution of the nonionic surfactant until the solution becomes visibly cloudy and then measuring the temperature.

The cloud point temperature can conveniently be determined automatically using the equipment and method described by Baum et al in Mat. Res. Std. 4 26 (1964).

Examples of suitable compounds functioning as activity enhancers, together with the respective elevated cloud point temperature obtained in each case when using the standard test defined hereinbefore are listed below in Table 1.

TABLE 1

Elevation of the cloud point temperature of a 0.025 M aqueous solution of polyoxyethylene(8)nonylphenyl ether in the presence of activity enhancers

| | 0.025 M aqueous solution of polyoxyethylene(8)nonyl phenyl ether (SYNPERONIC NP8 ex ICI) | |
|---|---|---|
| Activity Enhancer (5% by weight) | Cloud point temperature (°C.) | Elevation of cloud point temperature |
| None (control) | 33.5 | 0 |
| 2-methyl propan-2-ol | 55.0 | 21.5 |
| Propan-2-ol | 56.0 | 22.5 |
| Ethyl-hydroxypropanoate | 52.1 | 18.6 |
| Hexan-2,5-diol | 52.0 | 18.5 |
| POE(2) ethyl ether | 46.0 | 12.5 |
| Di(2-hydroxypropyl) ether | 44.8 | 11.3 |
| Pentan-2,4-diol | 48.0 | 14.5 |
| Acetone | 46.3 | 12.8 |
| POE(2) methyl ether | 43.5 | 10.0 |
| 2-hydroxypropionic acid | 45.0 | 11.5 |
| Propan-1-ol | 53.0 | 19.5 |
| 1,4 Dioxane | 44.0 | 10.5 |
| Tetrahydrofuran | 45.0 | 11.5 |
| Butan-1,4-diol | 45.0 | 11.5 |

OTHER INGREDIENTS

The composition according to the invention optionally can contain ingredients other than those already mentioned depending on the form of the intended product. It is, for example, possible to include antiseptics, preservatives, antioxidants, emulsifiers, colouring agents and detergents. It is also possible to include other materials which inluence hair regrowth such as minoxidil and derivatives thereof.

The composition according to the invention can also be employed as a vehicle for a wide variety of cosmetically or pharmaceutically active ingredients, particularly ingredients which have some beneficial effect when applied to the skin other than the promotion of hair growth.

The total amount of optional ingredients can form the balance of up to 84.99% by weight of the composition.

PROCESS FOR PREPARATION OF COMPOSITION

The invention also provides a process for the preparation of a composition suitable for topical application to mammalian skin, particularly to the hair and/or scalp of the human subject which comprises mixing an esterified oligosaccharide with a suitable cosmetically or physiologically acceptable vehicle, to provide a composition containing the oligosacchharide at a concentration of from 0.01 to 10% by weight.

FORM OF COMPOSITION

The composition of the invention can be formulated as liquids, for example as a lotion, shampoo, milk or cream for use in conjunction with an applicator such as a roll-ball applicator, or a spray device such as an aerosol can containing propellant, or a container fitted with a pump to dispense the liquid product. Alternatively, the composition of the invention can be solid or semi-solid, for example sticks, creams or gels, for use in conjunction with a suitable applicator or simply a tube, bottle or lidded jar, or as a liquid-impregnated fabric, such as a tissue wipe.

The invention accordingly also provides a closed container containing a composition as herein defined.

USE OF COMPOSITIONS

The invention also provides for the use of an esterified oligosaccharide in the topical treatment of baldness.

The compositions according to the invention are primarily intended for topical application to mammalian skin, particularly to the scalp of the human subject, especially where the head is already bald or balding. The compositions can also be applied prophilactically to the hair and hence the scalp to reduce or prevent the onset of baldness.

The amount of the composition and the frequency of application to the hair and/or scalp can vary widely, depending on personal needs, but it is suggested as an example that topical application of from 1 to 5 g daily containing from 0.001 to 1 g of a selected esterified oligosaccharide over the period of at least six months will in most cases result in an improvement in hair growth.

EFFICACY TESTING

The efficacy of the compositions according to the invention was examined using the rat as an animal model, in order to assess both the duration and amount of hair growth, following daily administration of such compositions.

For this purpose, hair was clipped from the treatment area at regular intervals and weighed as an index of hair production. The increased duration of anagen phase was apparent from growth curves obtained by plotting weight of hair recovered from clippings against duration of the experiment.

This model was validated using minoxidil, a compound known to stimulate hair growth, as a positive control.

Effective compounds were selected on the basis of their ability to increase hair production and to increase the duration of anagen phase, both of which are required attributes of any product for reversing baldness.

EXAMPLES

The invention is illustrated by the following examples:

EXAMPLE 1

This Example illustrates a lotion according to the invention which is suitable for topical application to the scalp in order to promote their growth.

The lotion has the following formulation:

|  | % w/w |
|---|---|
| disaccharide structure (53) | 0.1 |
| ethanol | 99.995 |
| perfume | q.s. |

EXAMPLE 2

This Example illustrates a hair tonic which is suitable for application to hair or scalp.

The hair tonic has the following formulation:

|  | % w/w |
|---|---|
| disaccharide:structure (54) | 0.8 |
| ethanol | 50 |
| water | 49 |
| perfume | q.s. |

EXAMPLE 3

This Example also illustrates a lotion which is suitable for topical application to the scalp.

The lotion has the following formulation:

|  | % w/w |
|---|---|
| disaccharide:structure (55) | 1.5 |
| propan-2-ol | 10 |
| ethanol | 88.5 |
| perfume | q.s. |

EXAMPLE 4

This Example also illustrates a hair tonic which is suitable for application to hair or scalp.

The hair tonic has the following formulation:

|  | % w/w |
|---|---|
| disaccharide:structure (56) | 0.2 |
| ethanol | 40 |
| water | 59.80 |
| perfume | q.s. |

EXAMPLES 5 TO 8

The following formulations represent lotions which can be used topically in the treatment of bald or balding male or female heads.

|  | % w/w | | | |
|---|---|---|---|---|
|  | 5 | 6 | 7 | 8 |
| Hydroxyethyl cellulose | 0.4 | — | 0.4 | — |
| Absolute ethanol | 25 | 25 | 25 | 25 |
| Propane-1,2-diol | — | — | 38.4 | 38.4 |
| Butane-1,3-diol | 38.4 | 38.8 | — | — |
| Paramethyl benzoate | 0.2 | 0.2 | 0.2 | 0.2 |
| Disaccharide structure (57) | 5 | — | — | — |
| Disaccharide structure (58) | — | 1 | — | — |
| Disaccharide structure (59) | — | — | 0.8 | — |
| Disaccharide structure (60) | — | — | — | 0.6 |
| Perfume | 1 | 1 | 1 | 1 |
| Water to | 100 | 100 | 100 | 100 |

EXAMPLES 9 TO 12

The following formulations represent creams which can be used in the treatment of baldness.

|  | % w/w | | | |
|---|---|---|---|---|
|  | 9 | 10 | 11 | 12 |
| Cetyl alcohol polyoxyethylene (10) | 4 | 4 | 4 | 4 |
| Cetyl alcohol | 4 | 4 | 4 | 4 |
| Mineral oil | 4 | 2 | — | — |
| Paraffin wax | — | 2 | 4 | — |
| Partial glyceride of palmitic and stearic acids | — | — | — | 4 |
| Disaccharide: structure (30) | 2 | — | — | — |
| Disaccharide: structure (61) | — | — | — | 1 |
| Disaccharide: structure (62) | — | 1.5 | — | — |
| Disaccharide: structure (63) | — | — | 2 | — |
| Triethanolamine | 0.75 | 0.75 | 0.75 | 0.75 |
| Butane-1,3-diol | 3 | 3 | 3 | 3 |
| Xanthan gum | 0.3 | 0.3 | 0.3 | 0.3 |
| Preservative | 0.4 | 0.4 | 0.4 | 0.4 |
| Perfume | q.s. | q.s. | q.s. | q.s. |
| Water to | 100 | 100 | 100 | 100 |

EXAMPLE 13

This Example illustrates a water-in-oil high internal phase emulsion containing a novel disaccharide according to the invention.

The emulsion consisted of 10% by volume oily phase and 90% by weight aqueous phase.

The oily phase and the aqueous phase had the following consitution:

|  | % w/w |
|---|---|
| Oily phase | |
| Sorbitan monooleate | 20 |
| Quartenium-18 hectorite | 5 |
| Liquid paraffin | 75 |
| Aqueous phase | |
| Disaccharide:structure (6) | 0.5 |
| Xanthan gum | 1 |

-continued

|  | % w/w |
|---|---|
| Preservative | 0.3 |
| Perfume | q.s. |
| Sodium chloride (1% w/w solution) to | 100 |

The emulsion was prepared by taking 10 parts by volume of the oily phase and to it adding slowly with stirring 90 parts by volume of the aqueous phase.

The high internal phase water-in-oil emulsion so formed can be applied topically to the scalp, to improve hair growth and regrowth.

The following examples 14 to 18 illustrate shampoos for use in washing the hair and scalp, and for promoting hair growth on the scalp.

EXAMPLE 14

|  | % w/w |
|---|---|
| Sodium lauryl ether sulphate (2 EO):21% AD | 41.4 |
| Lauryl dimethylamino acetic acid betaine* 30% AD | 4 |
| Coconut fatty acid diethanolamine | 1.5 |
| Oleyl triethoxy phosphate (BRIPHOS 03D) | 1 |
| Polyglycol-polyamine condensation resin (POLYQUART H):50% active | 1.5 |
| Preservative, colouring matter, salt | 0.58 |
| Disaccharide:structure (7) | 5 |
| Perfume | q.s. |
| Water to | 100 |

EXAMPLE 15

|  | % w/w |
|---|---|
| Sodium lauryl ether sulphate (2 EO): 100% AD | 12 |
| POLYQUART H:50% active | 2.5 |
| BRIPHOS 03D | 2.5 |
| Disaccharide:structure (8) | 4 |
| Perfume | q.s. |
| Water to | 100 |

EXAMPLE 16

|  | % w/w |
|---|---|
| Monoethanolamine lauryl sulphate: 100% AD | 20 |
| POLYQUART H:50% active | 3 |
| BRIPHOS 03D | 1.7 |
| Coconut diethanolamide | 5 |
| Disaccharide:structure (5) | 1 |
| Perfume | q.s. |
| Water to | 100 |
| pH adjusted to | 6.5 |

EXAMPLE 17

|  | % w/w |
|---|---|
| Sodium lauryl ether sulphate (3 EO): 100% AD | 12 |
| POLYQUART H:50% active | 0.3 |
| BRIPHOS 03D | 1 |
| Disaccharide:structure (10) | 2 |
| Perfume | q.s. |
| Water to | 100 |
| pH adjusted to | 6.5 |

EXAMPLE 18

|  | % w/w |
|---|---|
| Sodium lauryl ether sulphate (2 EO): 100% AD | 12 |
| POLYQUART H:50% active | 3 |
| BRIPHOS 03D | 1 |
| Opacifier | 9 |
| Disaccharide:structure (11) | 5 |
| Perfume | q.s. |
| Water to | 100 |
| pH adjusted to | 6.5 |

EXAMPLES 19 TO 24

The following Examples 19 to 24 illustrate powder compositions according to the invention which can be applied topically to the scalp.

|  | % w/w | | | | | |
|---|---|---|---|---|---|---|
|  | 19 | 20 | 21 | 22 | 23 | 24 |
| Chemically modified starch | 5 | — | 5 | — | 5 | — |
| Chemically modified cellulose | — | 5 | — | 5 | — | 5 |
| Boric acid | 10 | 10 | 10 | 10 | 10 | 10 |
| Zinc oxide | 5 | 5 | 5 | 5 | 5 | 5 |
| Disaccharide: structure (13) | 5 | — | — | — | — | — |
| Disaccharide: structure (15) | — | 10 | — | — | — | — |
| Disaccharide: structure (18) | — | — | 2 | — | — | — |
| Disaccharide: structure (17) | — | — | — | 4 | — | — |
| Disaccharide: structure (20) | — | — | — | — | 1 | — |
| Disaccharide: structure (22) | — | — | — | — | — | 3 |
| Perfume | q.s. | q.s. | q.s. | q.s. | q.s. | q.s. |
| Chalk | 10 | 10 | 10 | 10 | 10 | 10 |
| Talc to | 100 | 100 | 100 | 100 | 100 | 100 |

EXAMPLE 25

This Example illustrates a lotion according to the invention which is suitable for topical application to the scalp in order to promote hair growth.

The lotion has the following formulation:

|  | % w/w |
|---|---|
| disaccharide structure (24) | 0.1 |
| ethanol | 99.995 |
| perfume | q.s. |

EXAMPLE 26

This Example illustrates a hair tonic which is suitable for application to hair or scalp.

The hair tonic has the following formulation:

|  | % w/w |
|---|---|
| disaccharide:structure (25) | 0.9 |

|  | % w/w |
|---|---|
| ethanol | 50 |
| water | 49 |
| perfume | q.s. |

EXAMPLE 27

This Example also illustrates a lotion which is suitable for topical application to the scalp.
The lotion has the following formulation:

|  | % w/w |
|---|---|
| disaccharide:structure (27) | 1.5 |
| propan-2-ol | 10 |
| ethanol | 88.5 |
| perfume | q.s. |

EXAMPLE 28

This Example also illustrates a hair tonic which is suitable for application to hair or scalp.
The hair tonic has the following formulation:

|  | % w/w |
|---|---|
| disaccharide:structure (29) | 0.2 |
| ethanol | 40 |
| water | 59.80 |
| perfume | q.s. |

EXAMPLES 29 TO 32

The following formulations represent lotions which can be used topically in the treatment of bald or balding male or female heads.

|  | % w/w | | | |
|---|---|---|---|---|
|  | 29 | 30 | 31 | 32 |
| Hydroxyethyl cellulose | 0.4 | — | 0.4 | — |
| Absolute ethanol | 25 | 25 | 25 | 25 |
| Propane-1,2-diol | — | — | 38.4 | 38.4 |
| Butane-1,3-diol | 38.4 | 38.8 | — | — |
| Paramethyl benzoate | 0.2 | 0.2 | 0.2 | 0.2 |
| Disaccharide structure (30) | 5 | 1 | — | — |
| Disaccharide structure (31) | — | 1 | 4 | — |
| Disaccharide structure (32) | — | — | 1 | 3 |
| Disaccharide structure (33) | 2 | — | — | 3 |
| Perfume | 1 | 1 | 1 | 1 |
| Water to | 100 | 100 | 100 | 100 |

EXAMPLES 33 TO 36

The following formulations represent creams which can be used in the treatment of baldness.

|  | % w/w | | | |
|---|---|---|---|---|
|  | 33 | 34 | 35 | 36 |
| Cetyl alcohol polyoxyethylene (10) | 4 | 4 | 4 | 4 |
| Cetyl alcohol | 4 | 4 | 4 | 4 |
| Mineral oil | 4 | 2 | — | — |
| Paraffin wax | — | 2 | 4 | — |
| Partial glyceride | — | — | — | 4 |
| of palmitic and stearic acids | | | | |
| Disaccharide: structure (10) | 4 | — | 2 | — |
| Disaccharide: structure (11) | — | 5 | — | 1 |
| Disaccharide: structure (13) | — | 1.5 | — | 3.5 |
| Disaccharide: structure (18) | 2 | — | 2 | — |
| Triethanolamine | 0.75 | 0.75 | 0.75 | 0.75 |
| Butane-1,3-diol | 3 | 3 | 3 | 3 |
| Xanthan gum | 0.3 | 0.3 | 0.3 | 0.3 |
| Preservative | 0.4 | 0.4 | 0.4 | 0.4 |
| Perfume | q.s. | q.s. | q.s. | q.s. |
| Water to | 100 | 100 | 100 | 100 |

EXAMPLE 37

This Example illustrates a water-in-oil high internal phase emulsion containing a novel disaccharide according to the invention.

The emulsion consisted of 10% by volume oily phase and 90% by weight aqueous phase.

The oily phase and the aqueous phase had the following consitution:

|  | % w/w |
|---|---|
| Oily phase | |
| Sorbitan monooleate | 20 |
| Quartenium-18 hectorite | 5 |
| Liquid paraffin | 75 |
| Aqueous phase | |
| Disaccharide:structure (36) | 0.5 |
| Xanthan gum | 1 |
| Preservative | 0.3 |
| Perfume | q.s. |
| Sodium chloride (1% w/w solution) to | 100 |

The emulsion was prepared by taking 10 parts by volume of the oily phase and to it adding slowly with stirring 90 parts by volume of the aqueous phase.

The high internal phase water-in-oil emulsion so formed can be applied topically to the scalp, to improve hair growth and regrowth.

The following examples 38 to 42 illustrate shampoos for use in washing the hair and scalp, and for promoting hair growth on the scalp.

EXAMPLE 38

|  | % w/w |
|---|---|
| Sodium lauryl ether sulphate (2 EO):21% AD | 41.4 |
| Lauryl dimethylamino acetic acid betaine:30% AD | 4 |
| Coconut fatty acid diethanolamine | 1.5 |
| Oleyl triethoxy phosphate (BRIPHOS 03D) | 1 |
| Polyglycol-polyamine condensation resin (POLYQUART H):50% active | 1.5 |
| Preservative, colouring matter, salt | 0.58 |
| Disaccharide:structure (37) | 5 |
| Perfume | q.s. |
| Water to | 100 |

EXAMPLE 39

|  | % w/w |
|---|---|
| Sodium lauryl ether sulphate (2 EO): 100% AD | 12 |
| POLYQUART H: 50% active | 2.5 |
| BRIPHOS 03D | 2.5 |
| Disaccharide: structure (15) | 4 |
| Perfume | q.s. |
| Water to | 100 |

EXAMPLE 40

|  | % w/w |
|---|---|
| Monoethanolamine lauryl sulphate: 100% AD | 20 |
| POLYQUART H: 50% active | 3 |
| BRIPHOS 03D | 1.7 |
| Coconut diethanolamide | 5 |
| Disaccharide: structure (56) | 1 |
| Perfume | q.s. |
| Water to | 100 |
| pH adjusted to 6.5 | |

EXAMPLE 41

|  | % w/w |
|---|---|
| Sodium lauryl ether sulphate (3 EO): 100% AD | 12 |
| POLYQUART H: 50% active | 0.3 |
| BRIPHOS 03D | 1 |
| Disaccharide: structure (57) | 2 |
| Perfume | q.s. |
| Water to | 100 |
| pH adjusted to 6.5 | |

EXAMPLE 42

|  | % w/w |
|---|---|
| Sodium lauryl ether sulphate (2 EO): 100% AD | 12 |
| POLYQUART H: 50% active | 3 |
| BRIPHOS 03D | 1 |
| Opacifier | 9 |
| Disaccharide: structure (58) | 5 |
| Perfume | q.s. |
| Water to | 100 |
| pH adjusted to 6.5 | |

EXAMPLES 43 TO 47

The following Examples 43 to 47 illustrate powder compositions according to the invention which can be applied topically to the scalp.

| | % w/w | | | | |
|---|---|---|---|---|---|
| | 43 | 44 | 45 | 46 | 47 |
| Chemically modified starch | 5 | — | 5 | — | 5 |
| Chemically modified cellulose | — | 5 | — | 5 | — |
| Boric acid | 10 | 10 | 10 | 10 | 10 |
| Zinc oxide | 5 | 5 | 5 | 5 | 5 |
| Disaccharide: structure (59) | 5 | — | — | — | — |
| Disaccharide: structure (60) | — | 10 | — | — | — |
| Disaccharide: structure (61) | — | — | 2 | — | — |
| Disaccharide: structure (62) | — | — | — | 4 | — |
| Disaccharide: structure (63) | — | — | — | — | 1 |
| Perfume | q.s. | q.s. | q.s. | q.s. | q.s. |
| Chalk | 10 | 10 | 10 | 10 | 10 |
| Talc to | 100 | 100 | 100 | 100 | 100 |

We claim:

1. An esterified oligosaccharide including at least one esterified disaccharide unit consisting of a uronic acid residue having the structure:

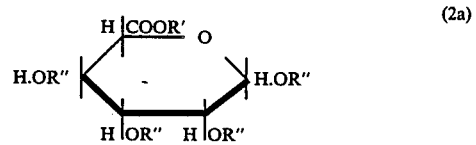
(2a)

and a hexosamine residue having the structure:

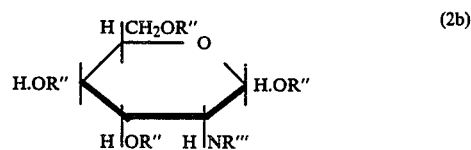
(2b)

where
R' is $C_3$ to $C_{10}$ alkyl or

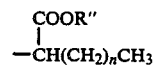

R" is —H, $C_1$ to $C_4$ alkyl, —CO(CH$_2$)$_m$CH$_3$, —SO$_3$M
R''' is —H, —CO(CH$_2$)$_m$CH$_3$, or —SO$_3$M
M is —H, or a metallic or organic cation
n is 0 or an integer of from 1 to 7
m is 0 or the integer 1 or 2
the groups designated R" being the same or different, one R" group from each pyranose ring structure being linked by a glycosidic linkage having the configuration α-1,3; α-1,4; β-1,3; or β-1,4; and the —COOR', —CH$_2$OR" and —OR" groups being of either configuration with respect to the pyranose rings;
provided that when the esterified oligosaccharide is an esterified disaccharide unit having the structure:

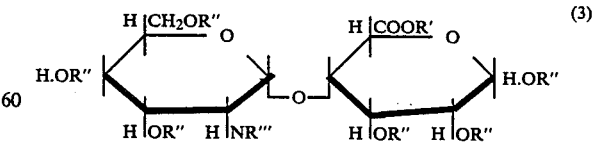
(3)

then R' is $C_5$ to $C_{10}$ alkyl or

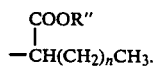

2. The esterified oligosaccharide of claim 1 having the generic structure:

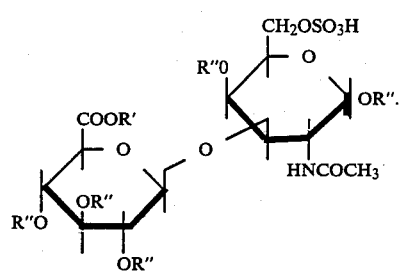
(4)

3. The esterified oligosaccharide of claim 2, selected from those having the following structures:

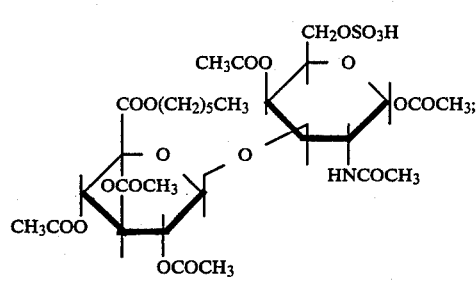
(5)

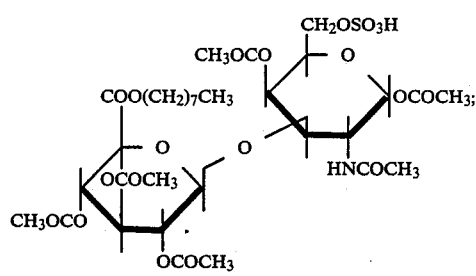
(6)

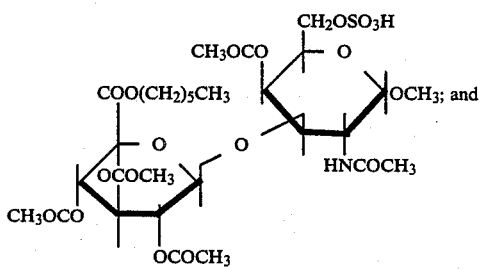
(7)

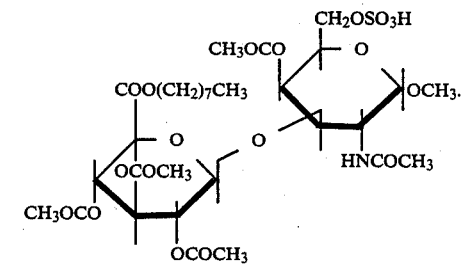
(8)

4. The esterified oligosaccharide of claim 1 having the generic structure:

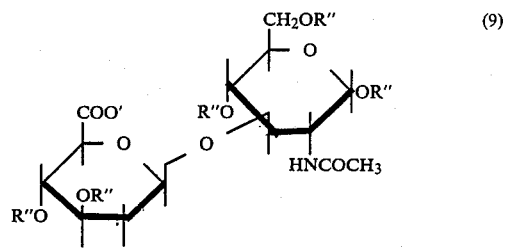
(9)

5. The esterified oligosaccharide of claim 4, selected from those having the structures:

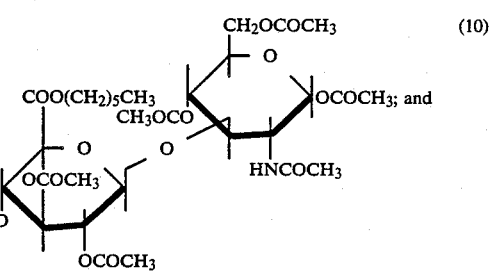
(10)

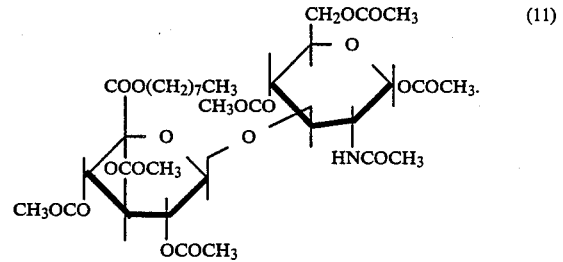
(11)

6. the esterified oligosaccharide of claim 1 having the generic structure:

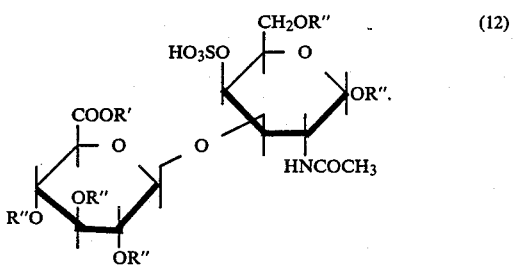
(12)

7. The esterified oligosaccharide of claim 6 having the structure:

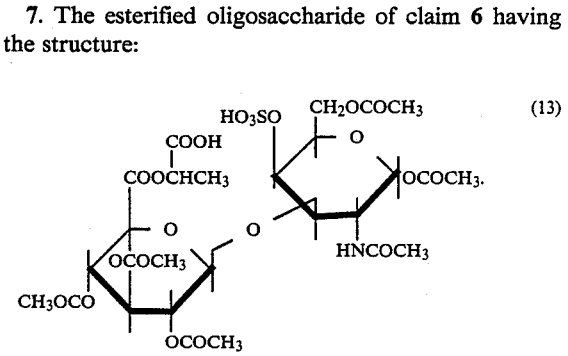
(13)

8. The esterified oligosaccharide of claim 1 having the generic structure:

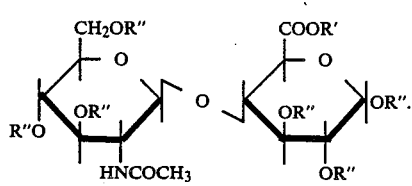 (14)

9. The esterified oligosaccharide of claim 8 having the structure:

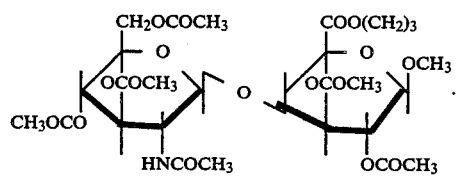 (15)

10. The esterified oligosaccharide of claim 1 having the generic structure:

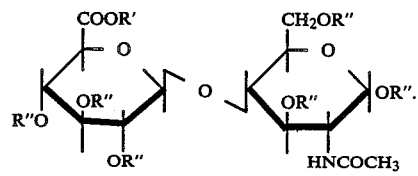 (16)

11. The esterified oligosaccharide of claim 10 selected from those having the structure:

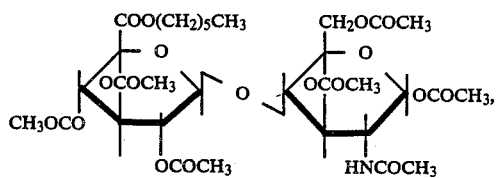 (17)

and

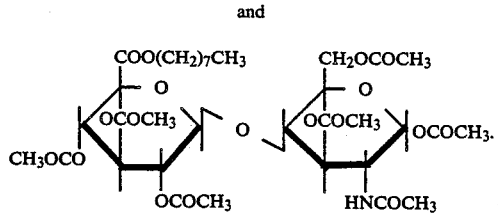 (18)

12. The esterified oligosaccharide of claim 1 having the generic structure:

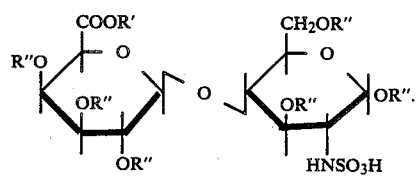 (19)

13. The esterified oligosaccharide of claim 12 having the structure:

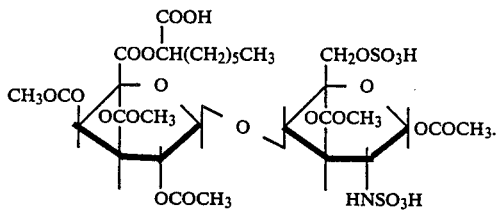 (20)

14. The esterified oligosaccharide of claim 1 having the generic structure:

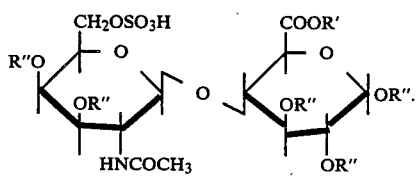 (21)

15. The esterified oligosaccharide of claim 14, having the structure:

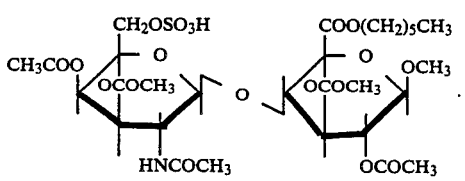 (22)

16. The esterified oligosaccharide of claim 1 having the generic structure:

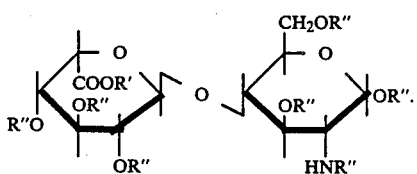 (23)

17. The esterified oligosaccharide of claim 16, selected from those having the structure:

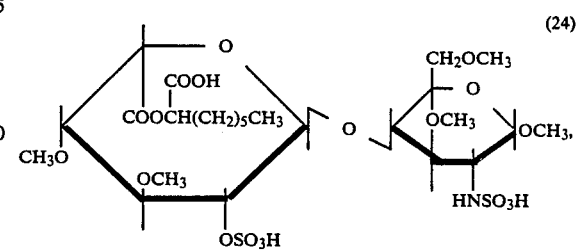 (24)

and

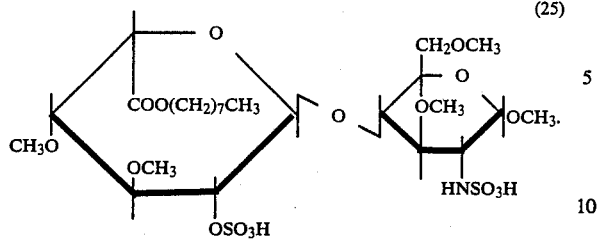
(25)

18. The esterified oligosaccharide of claim 1 having the generic structure:

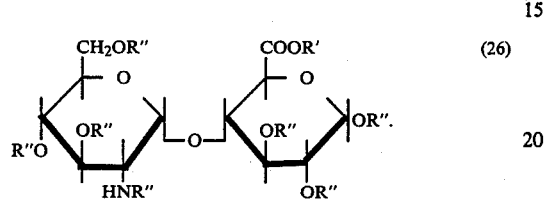
(26)

19. The esterified oligosaccharide of claim 18 having the structure:

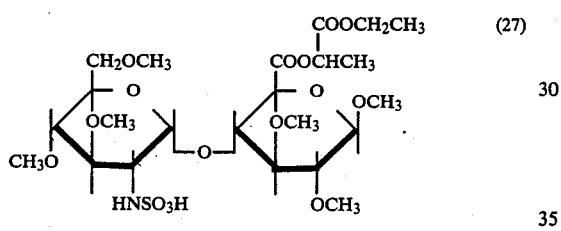
(27)

20. The esterified oligosaccharide of claim 1 having the generic structure:

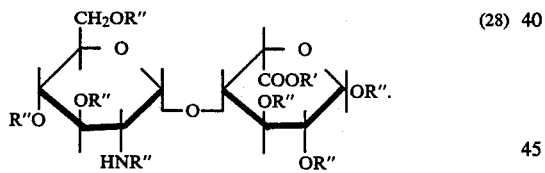
(28)

21. The esterified oligosaccharide of claim 20, having the structure:

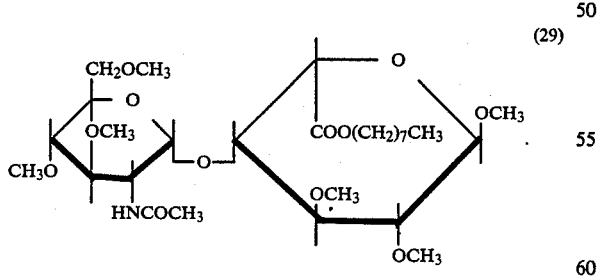
(29)

22. A process for the synthesis of an esterified oligosaccharide as defined in claim 1, which comprises the steps of:
  (i) subjecting a glycosaminoglycan chain to chemical cleavage to yield oligosaccharide fragments containing at least one disaccharide unit comprising a hexosamine residue having the structure:

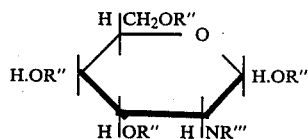
(2b)

which is glycosidically linked to the C-1 position of a uronic acid residue having the structure:

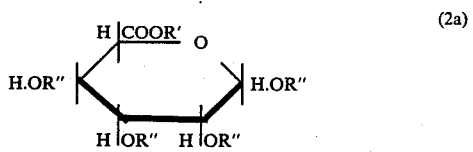
(2a)

and
  (ii) modifying the oligosaccharide fragments by one or more process steps in any sequence chosen from:
  acylation of free hydroxyl groups,
  acylation of free amino groups,
  sulphation of free hydroxyl groups,
  sulphation of free amino groups,
  esterification of free hydroxyl groups, and
  etherification of free hydroxyl groups;
  to provide the esterified oligosaccharide.

23. The process of claim 22, for the synthesis of the esterified disaccharide having the structure (5), which process comprises the steps of:
  (i) subjecting the glycosaminoglycan chondroitin sulphate to acid hydrolysis to yield the disaccharide chondrosine having the structure:

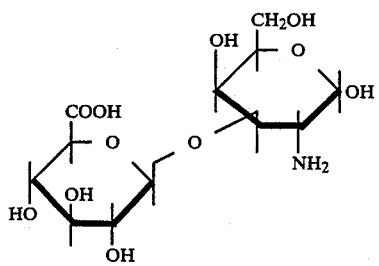

(ii) subjecting the chondrosine to N-acetylation to yield N-acetylchondrosine having the structure:

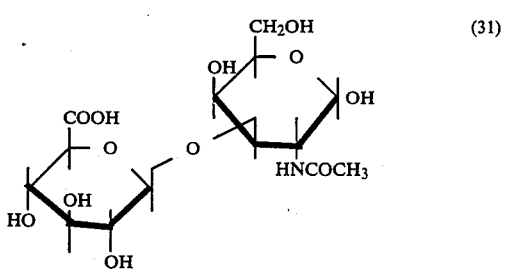
(31)

(iii) subjecting the N-acetylchondrosine to sulphation in the C-6 position of the hexosamine moiety to yield N-acetylchondrosine-6-O-sulphate having the structure:

(iv) subjecting the N-acetylchondrosine-6-O-sulphate to esterification to yield the intermediate product having the structure:

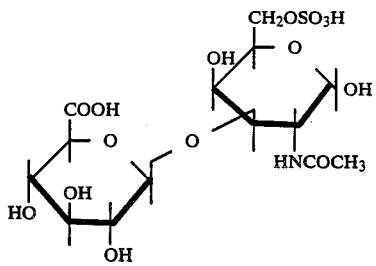

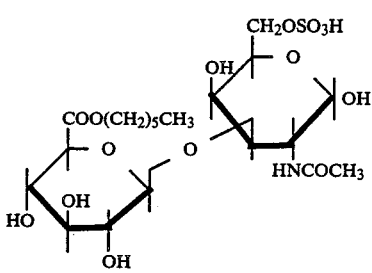

and (v) subjecting the intermediate product having the structure (33) to full acetylation to yield the esterified disaccharide having the structure:

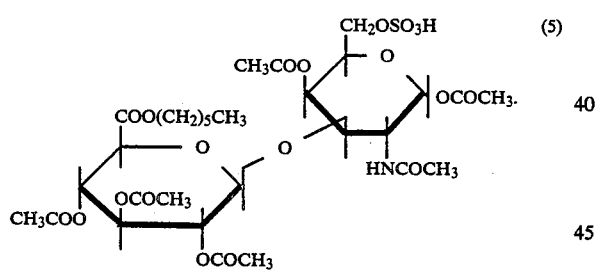

24. A process for the synthesis of an esterified oligosaccharide as defined in claim 1 having at least one uronic acid residue linked in the β configuration through the C-1 position to a hexosamine residue, or having at least one hexosamine residue linked in the α or β configuration through the C-1 position to a uronic acid residue, which process comprises the steps of:

(i) condensing a hexosamine residue having the structure:

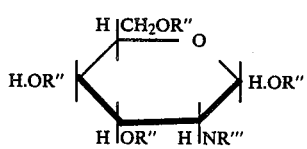

with a uronic acid residue having the structure:

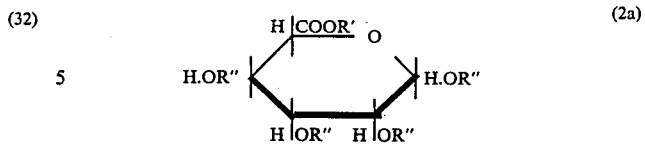

to form an oligosaccharide intermediate, the functional groups of which residues have been modified or protected in such a way that glycosidic bond formation can only occur between the C-1 position of one residue and a free hydroxyl group in the C-3 or C-4 position of the other residue, the α or β configuration of the glycosidic linkage so formed being dictated by the nature of the leaving group on the C-1 position; and (ii) removal of at least one protecting group from the oligosaccharide intermediate by one or more process steps in any sequence chosen from:
reduction,
acid catalysis, and
base catalysis;
to provide the esterified oligosaccharide.

25. The process of claim 24 for the synthesis of the esterified disaccharide having the structure (15), which process comprises the steps of:

(i) condensing the oxazoline derivative of N-acetylglucosamine having the structure:

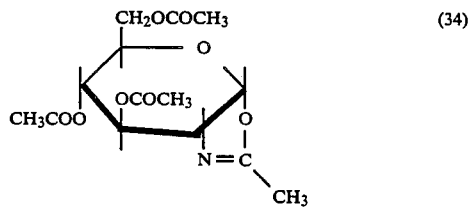

with the benzylated uronic acid moiety having the structure:

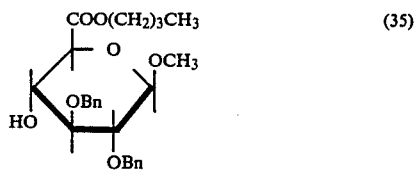

in the presence of nitromethane and p-toluene sulphonic acid to yield the benzylated β-1,4 disaccharide having the structure:

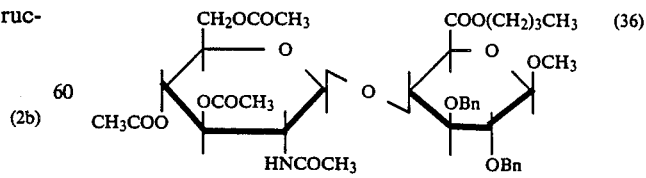

(ii) hydrogenating the benzylated β-1,4 disaccharide to remove the benzyl groups to yield a β-1,4 partially acetylated disaccharide having the structure:

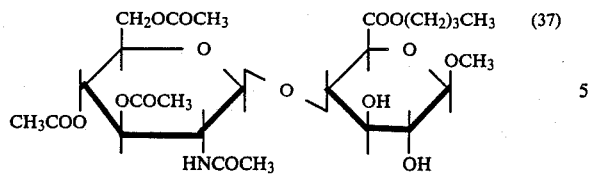

and, (iii) acetylating the partially acetylated β-1,4 disaccharide to yield the fully acetylated β-1,4 disaccharide having the structure:

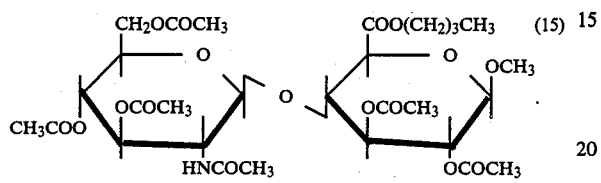

26. A composition suitable for topical application to mammalian skin comprising an effective amount of from 0.01 to 10% by weight of an esterified oligosaccharide as defined in claim 1, together with from 10 to 99.99% by weight of a cosmetically or physiologically acceptable carrier.

27. A composition suitable for topical application to mammalian skin comprising an effective amount of from 0.01 to 10% by weight of an esterified disaccharide including a uronic acid residue having the structure:

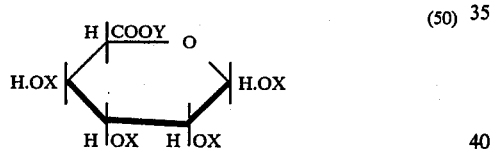

and a hexosamine residue having the structure:

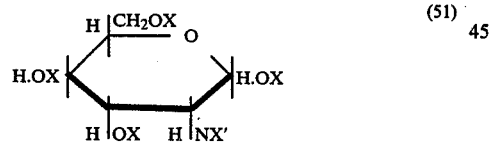

where

X is —H, $C_1$ to $C_4$ alkyl, —CO(CH$_2$)$_m$CH$_3$, —SO$_3$M, or an aryl radical, X is —H, —CO(CH$_2$)$_m$CH$_3$, or —SO$_3$M, Y is —H, $C_1$ to $C_4$ alkyl or M, and M is —H or a metallic or organic cation, and m is O or the integer 1 or 2;

the groups designated X being the same or different, one —OH group from each pyranose ring structure being linked by a glycosidic linkage having the configuration α-1,3, β-1,3, α-1,4 or β-1,4; and the —COOY, —CH$_2$OX and —OX groups being of either configuration with respect to the pyranose ring;

together with from 10 to 99.99% by weight of a cosmetically or physiologically acceptable carrier.

28. The composition of claim 27 in which the esterified disaccharide has the structure:

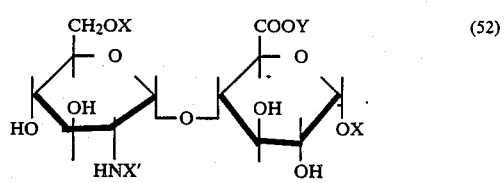

29. The composition of claim 28, in which the esterfied disaccharide in selected from those having the following structures:

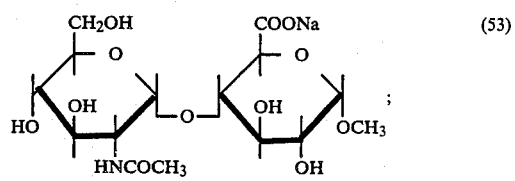

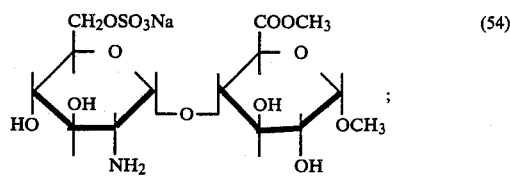

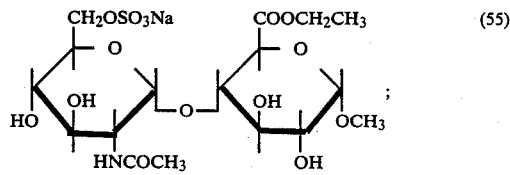

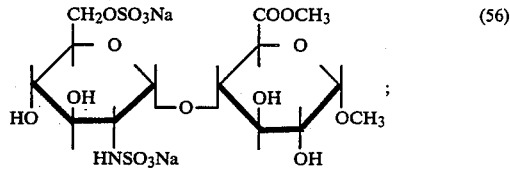

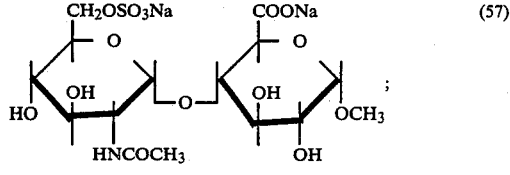

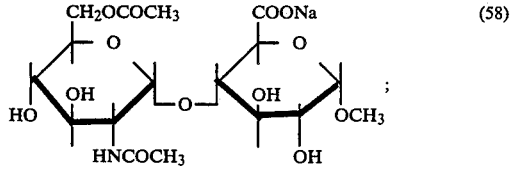

and

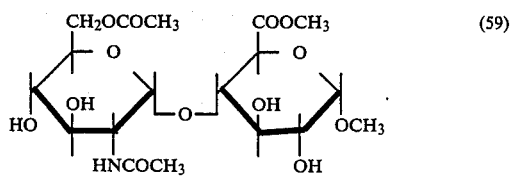

30. The composition of claim 27, in which the esterfied disaccharide is selected from those having the following structure:

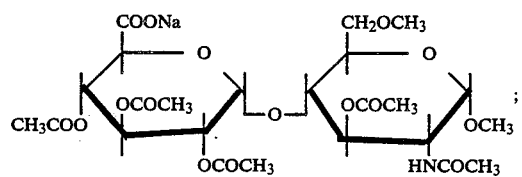 (60)

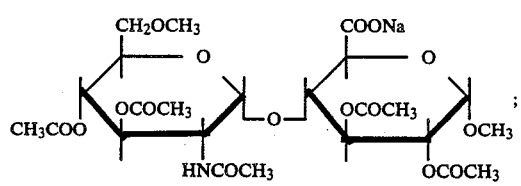 (61)

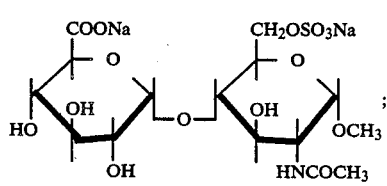 (62)

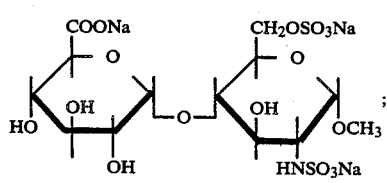 (63)

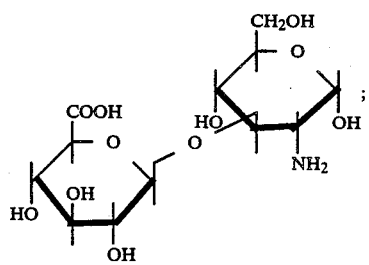 (64)

-continued

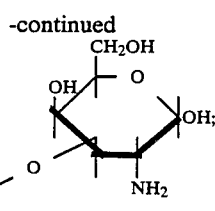 (30)

 (31)

and

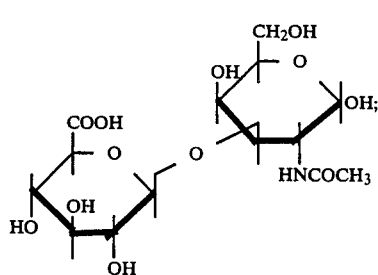 (32)

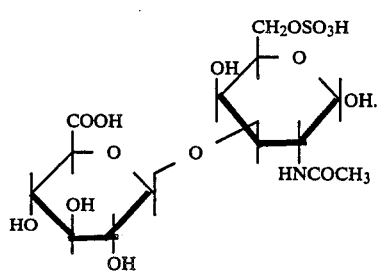

31. A composition suitable for topical application to mammalian skin comprising an effective amount of from 0.01 to 10% by weight of a low molecular weight limit enzymic digest comprising an esterified oligosaccharide derived from a glycosaminoglycan chosen from heparan sulphate, hyaluronic acid and chondroitin sulphate.

32. A method for the conversion of vellus hair to growth as terminal hair, which comprises applying to mammalian skin in the region of vellus hair, an effective amount of the composition of claim 26.

33. A method for the conversion of vellus hair to growth as terminal hair, which comprises applying to mammalian skin in the region of vellus hair, an effective amount of the composition of claim 27.

34. A method for increasing the rate of terminal hair growth in mammalian species, which comprises applying to mammalian skin in the region of terminal hair, an effective amount of the composition of claim 26.

35. A method for increasing the rate of terminal hair growth in mammalian species, which comprises applying to mammalian skin in the region of terminal hair, an effective amount of the composition of claim 27.

36. The use of the esterified oligosaccharide as defined in claim 1 in the promotion of mammalian hair growth or regrowth.

* * * * *